United States Patent
Lutz et al.

(10) Patent No.: US 10,207,225 B2
(45) Date of Patent: Feb. 19, 2019

(54) SINGLE-PASS FILTRATION SYSTEMS AND PROCESSES

(71) Applicant: EMD Millipore Corporation, Burlington, MA (US)

(72) Inventors: Herbert Lutz, Playa del Rey, CA (US); Joseph Parrella, Westford, MA (US); Bala Raghunath, Bangalore (IN)

(73) Assignee: EMD Millipore Corporation, Burlington, MA (US)

( * ) Notice: Subject to any disclaimer, the term of this patent is extended or adjusted under 35 U.S.C. 154(b) by 0 days.

(21) Appl. No.: 14/736,646

(22) Filed: Jun. 11, 2015

(65) Prior Publication Data

US 2015/0360180 A1 Dec. 17, 2015

Related U.S. Application Data

(60) Provisional application No. 62/012,792, filed on Jun. 16, 2014.

(51) Int. Cl.
*C07K 1/34* (2006.01)
*B01D 61/14* (2006.01)
(Continued)

(52) U.S. Cl.
CPC ......... *B01D 61/145* (2013.01); *B01D 61/142* (2013.01); *B01D 61/18* (2013.01); *B01D 63/082* (2013.01); *B01D 65/02* (2013.01); *B01D 2313/18* (2013.01); *B01D 2315/10* (2013.01); *B01D 2319/022* (2013.01);
(Continued)

(58) Field of Classification Search
None
See application file for complete search history.

(56) References Cited

U.S. PATENT DOCUMENTS

| | | | |
|---|---|---|---|
| 3,540,595 A | 11/1970 | Edwards | |
| 4,222,874 A | 9/1980 | Connelly | |

(Continued)

FOREIGN PATENT DOCUMENTS

| | | |
|---|---|---|
| CN | 103429308 | 12/2013 |
| EP | 0 307 047 | 9/1988 |

(Continued)

OTHER PUBLICATIONS

Zou, Y., et al., "New Technologies for high concentration protein ultrafiltration: High Viscosity TFF Cassettes and Single-Pass TFF", 2014, EMD Millipore, 1 pg.

(Continued)

*Primary Examiner* — Krishnan S Menon
(74) *Attorney, Agent, or Firm* — Hamilton, Brook, Smith & Reynolds, P.C.

(57) ABSTRACT

The present invention provides, in various embodiments, hybrid single-pass tangential flow filtration assemblies, disposable single-pass tangential flow filtration assemblies, scalable single-pass tangential flow filtration assemblies and adaptable modular single-pass tangential flow filtration assemblies. In other embodiments, the invention relates to processes for recovering proteins from the surface of a filtration membrane in a single-pass tangential flow filtration assembly and for cleaning a tangential flow filtration assembly. In additional embodiments, the invention provides methods of increasing the processing capacity of a single-pass tangential flow filtration assembly.

21 Claims, 9 Drawing Sheets

(51) Int. Cl.
*B01D 61/18* (2006.01)
*B01D 63/08* (2006.01)
*B01D 65/02* (2006.01)

(52) U.S. Cl.
CPC ...... B01D 2319/04 (2013.01); B01D 2321/04 (2013.01); B01D 2321/06 (2013.01); B01D 2321/164 (2013.01); C07K 1/34 (2013.01); Y10T 29/49828 (2015.01)

(56) References Cited

U.S. PATENT DOCUMENTS

| | | |
|---|---|---|
| 4,756,835 A | 7/1988 | Wilson |
| 4,765,906 A | 8/1988 | Downing et al. |
| 4,956,085 A | 9/1990 | Kopf |
| D325,070 S | 3/1992 | Kopf |
| D327,313 S | 6/1992 | Kopf |
| 5,147,542 A | 9/1992 | Proulx |
| D357,059 S | 4/1995 | Kopf |
| 5,470,468 A | 11/1995 | Colby |
| 5,538,642 A | 7/1996 | Solie |
| 5,599,447 A | 2/1997 | Pearl et al. |
| 5,654,025 A | 8/1997 | Raghunath et al. |
| 5,685,990 A | 11/1997 | Saugmann et al. |
| 6,139,746 A | 10/2000 | Kopf |
| 6,294,090 B1 | 9/2001 | Nussbaumer et al. |
| 6,365,395 B1 | 4/2002 | Chris |
| 6,387,270 B1 | 5/2002 | van Reis |
| 6,596,172 B1 | 7/2003 | Kopf |
| 6,926,833 B2 | 8/2005 | van Reis |
| 7,101,561 B2 | 9/2006 | Maertens et al. |
| 7,384,549 B2 | 6/2008 | de los Reyes et al. |
| 7,531,632 B2 | 5/2009 | Perreault |
| 7,682,511 B2 | 3/2010 | de los Reyes et al. |
| 7,959,805 B2 | 6/2011 | Chisolm et al. |
| 7,967,987 B2 | 6/2011 | de los Reyes et al. |
| D651,280 S | 12/2011 | Okawa et al. |
| D655,780 S | 3/2012 | Honda et al. |
| 8,157,999 B2 | 4/2012 | de los Reyes et al. |
| 8,231,787 B2 | 7/2012 | Mir et al. |
| 8,506,802 B1 | 8/2013 | de los Reyes |
| 8,728,315 B2 | 5/2014 | de los Reyes et al. |
| 8,747,669 B1 | 6/2014 | Bonner et al. |
| D729,897 S | 5/2015 | Ledbetter et al. |
| 9,133,433 B2 | 9/2015 | Vogel et al. |
| D741,983 S | 10/2015 | Mueller et al. |
| D762,811 S | 8/2016 | Natale et al. |
| D811,519 S | 2/2018 | Natale et al. |
| 2002/0177693 A1 | 11/2002 | Lebing et al. |
| 2003/0066794 A1 | 4/2003 | Diel |
| 2003/0111402 A1 | 6/2003 | Baig et al. |
| 2004/0167320 A1 | 8/2004 | Couto et al. |
| 2005/0184008 A1 | 8/2005 | Schacht |
| 2005/0197496 A1 | 9/2005 | Perreault |
| 2006/0051347 A1 | 3/2006 | Winter |
| 2006/0144788 A1 | 7/2006 | Cath et al. |
| 2007/0173638 A1 | 7/2007 | Buchacher et al. |
| 2007/0246406 A1 | 10/2007 | Dibel et al. |
| 2008/0135500 A1 | 6/2008 | Gagnon et al. |
| 2009/0145838 A1 | 6/2009 | Knappe et al. |
| 2009/0214522 A1 | 8/2009 | Winter |
| 2009/0266756 A1 | 10/2009 | Fischer-Fruehholz et al. |
| 2010/0111378 A1 | 5/2010 | Kwan |
| 2011/0005984 A1 | 1/2011 | Boettcher et al. |
| 2011/0309018 A1 | 12/2011 | Kopf et al. |
| 2012/0077963 A1 | 3/2012 | Hongo et al. |
| 2012/0122076 A1 | 5/2012 | Lau et al. |
| 2012/0166332 A1 | 6/2012 | Naaman |
| 2012/0264948 A1 | 10/2012 | Hilbert et al. |
| 2012/0298578 A1 | 11/2012 | Herrington et al. |
| 2012/0316323 A1 | 12/2012 | Nardini et al. |
| 2013/0037486 A1 | 2/2013 | Sayer et al. |
| 2013/0146531 A1 | 6/2013 | Tayalia et al. |
| 2013/0334128 A1 | 12/2013 | Takagi et al. |
| 2014/0231331 A1 | 8/2014 | de los Reyes et al. |
| 2014/0251896 A1 | 9/2014 | Hirozawa |
| 2015/0144560 A1 | 5/2015 | Taniguchi et al. |
| 2015/0361129 A1 | 12/2015 | Natarajan et al. |
| 2015/0375173 A1 | 12/2015 | Steen |
| 2016/0059159 A1 | 3/2016 | Steen et al. |
| 2016/0059160 A1 | 3/2016 | Steen et al. |
| 2017/0056825 A1 | 3/2017 | Schwan et al. |
| 2017/0157566 A1 | 6/2017 | Gefroh et al. |

FOREIGN PATENT DOCUMENTS

| | | |
|---|---|---|
| EP | 613 724 | 3/1989 |
| EP | 1 029 583 | 8/2000 |
| EP | 1 707 254 | 3/2006 |
| EP | 1 974 801 A2 | 1/2008 |
| EP | 2 067 522 | 5/2008 |
| EP | 1 944 076 A1 | 7/2008 |
| EP | 2 119 492 | 11/2009 |
| EP | 2 682 168 | 1/2014 |
| EP | 2 703 066 | 3/2014 |
| EP | 2735357 | 5/2014 |
| JP | 2000288541 A | 10/2000 |
| JP | 2001252543 | 9/2001 |
| JP | 2008023415 | 2/2008 |
| JP | 2009178915 | 8/2009 |
| JP | 2010-053154 | 3/2010 |
| JP | 2013240765 | 5/2013 |
| WO | WO 2000/048703 | 8/2000 |
| WO | WO 2005/054287 | 6/2005 |
| WO | WO 2007/076496 | 7/2007 |
| WO | WO 2007/076497 | 7/2007 |
| WO | WO 2009/064797 | 5/2009 |
| WO | WO 2011/094236 | 8/2011 |
| WO | WO 2012/039675 A1 | 3/2012 |
| WO | 2013047746 A1 | 4/2013 |
| WO | WO 2013/047744 | 4/2013 |
| WO | 2013106337 A1 | 7/2013 |
| WO | WO 2013/125505 | 8/2013 |
| WO | WO 2014/067898 | 5/2014 |
| WO | 2015133972 A1 | 9/2015 |
| WO | WO 2015/195452 | 12/2015 |
| WO | WO 2015/195453 | 12/2015 |
| WO | WO 2015/200691 A1 | 12/2015 |
| WO | WO 2016/033546 | 3/2016 |
| WO | WO 2016/033553 | 3/2016 |

OTHER PUBLICATIONS

Pall Corporation Brochure "Cadence™ Single-Pass Tangential Flow Filtration Modules and Systems", (2014).
Notification Concerning Transmittal of International Preliminary Report on Patentability for International Application No. PCT/US2015/035250, "Single-Pass Filtration Systems and Processes", dated Dec. 29, 2016.
Notification Concerning Transmittal of International Preliminary Report on Patentability for International Application No. PCT/US2015/035251, "Methods for Increasing the Capacity of Flow-Through Processes", dated Dec. 29, 2016.
Notification Concerning Transmittal of International Preliminary Report on Patentability for International Application No. PCT/US2015/037780, "Compact Spiral-Wound Filter Elements, Modules and Systems", dated Jan. 5, 2017.
Non-Final Office Action dated Jan. 27, 2017 for U.S. Appl. No. 14/750,838, "Compact Spiral-Wound Filter Elements, Modules and Systems".
Casey et al., "Cadence Single-pass TFF Coupled with Chromatography Steps Enables Continuous Bioprocessing while Reducing Processing Times and Volumes," Retrieved from the internet: URL: www.pall.com/pdfs/Biopharmaceuticals/USD3003_Cadence_SPTFF_ChromSteps_AN.pdf, Retrieved on: Dec. 8, 2015, whole document.
Casey et al., "Protein concentration with single-pass tangential flow filtration (SPTFF)," *Journal of Membrane Science*, 384(1): 82-88 (Sep. 2011).
Casey, C. et al., "CadenceTM Single-pass TFF Coupled with Chromatography Steps Enables Continuous BioProcessing while Reducing Processing Times and Volumes", Application Note (Jan. 2015).

(56) References Cited

OTHER PUBLICATIONS

Chinese Search Report for CN Application No. 201580000755.4, "Processes for Filtering Liquids Using Single Pass Tangential Flow Filtration Systems and Tangential Flow Filtration Systems With Recirculation of Retentate", dated Oct. 27, 2016.
Choo, K.-H. and C.-H. Lee, "Membrane fouling mechanisms in the membrane-coupled anaerobic bioreactor," Water Research, 30(8): 1771-1780 (Aug. 1996).
Dizon-Maspat, J. et al., "Single pass tangential flow filtration to debottleneck downstream processing for therapeutic antibody production," *Biotechnology and Bioengineering*, 109(4): 962-970 (Apr. 2012).
Extended European Search Report for EP Application No. 15172144.6, titled: Single-Pass Filtration Systems and Processes, dated: Nov. 20, 2015.
International Search Report and Written Opinion for International Application No. PCT/US2015/037780, "Compact Spiral-Wound Filter Elements, Modules and Systems", dated Sep. 7, 2015.
International Search Report and Written Opinion for Int'l Application No. PCT/US2015/035251, titled: Methods for Increasing the Capacity of Flow-Through Processes, dated Dec. 18, 2015.
International Search Report and Written Opinion for Int'l Application No. PCT/US2015/035250, titled: Single-Pass Filtration Systems and Processes, dated Dec. 14, 2015.
International Search Report and Written Opinion for Int'l Application No. PCT/US2015/047574, titled: Single Pass Tangential Flow Filtration Systems and Tangential Flow Filtration Systems With Recirculation of Retentate, dated Dec. 7, 2015.
International Search Report and Written Opinion for Int'l Application No. PCT/US2015/047585, titled: Processes for Filtering Liquids Using Single Pass Tangential Flow Filtration Systems and Tangential Flow Filtration Systems With Recirculation of Retentate, dated Dec. 7, 2015.
Kwang-Ho, C. et al., "Membrane fouling mechanisms in the membrane-coupled anaerobic bioreactor," *Water Research*, 30(8): 1771-1780 (Aug. 1996).
Liu, H.F., et al., "Recovery and purification process development for monoclonal antibody production," mAbs 2(5):480-499 (Sep. 1, 2010).
Maintenance Procedures PelliconTM and PelliconTM-2 Cassette Filters (Jul. 1998).
Middlewood, P.G. et al., "Extraction of amaranth starch from an aqueous medium using microfiltration: Membrane fouling and cleaning," *Journal of Membrane Science*, vol. 411-412, pp. 22-29 (Apr. 2012).
Partial European Search Report for EP Application No. 15172146.1, titled: "Compact Spiral-Wound Filter Elements, Modules and Systems", dated Nov. 6, 2015.
Rathore, A.S. et al., "Recent Developments in Membrane-Based Separations in Biotechnology Processes: Review," *Preparative Biochemistry and Biotechnology*, 41(4): 398-421 (Oct. 2011).
Teske et al., "Inline Ultrafiltration," *Biotechnol. Prog.*, 26(4): 1068-1072 (Mar. 2010).
van Reis, R. et al., "Linear Scale Ultrafiltration," *Biotechnology and Bioengineering*, 55(5): 737-746 (Sep. 1997).
Steen et al., "Single Pass Tangential Flow Filtration", ACS mtg. poster, Anaheim, CA Mar. 2011.
Notification Concerning Transmittal of International Preliminary Report on Patentability for International Application No. PCT/US2015/047574, "Single Pass Tangential Flow Filtration Systems and Tangential Flow Filtration Systems With Recirculation of Retentate", dated Mar. 9, 2017.
Schwartz, L., "Diafiltration for Desalting or Buffer Exchange," BioProcess International, pp. 43-49 (2003).
Notification Concerning Transmittal of International Preliminary Report on Patentability for International Application No. PCT/US2015/047585, "Processes for Filtering Liquids Using Single Pass Tangential Flow Filtration Systems and Tangential Flow Filtration Systems With Recirculation of Retentate", dated Mar. 9, 2017.
Internet blog, Tangential Flow Filtration http://blog.naver.com/amiconls/23855658 (Apr. 26, 2006).
Chinese Search Report for CN Application No. 201580000755.4, "Single Pass Tangential Flow Filtration Systems and Tangential Flow Filtration Systems With Recirculation of Retentate", dated Mar. 24, 2017.
Singapore Search Report and Written Opinion for SG Application No. 10201504670R, "Single-Pass Filtration Systems and Processes", dated Nov. 22, 2017.

SINGLE-PASS FILTRATION SYSTEMS AND PROCESSES

RELATED APPLICATION(S)

This application claims the benefit of U.S. Provisional Application No. 62/012,792, filed on Jun. 16, 2014. The entire teachings of the above application is incorporated herein by reference.

BACKGROUND OF THE INVENTION

Single-pass tangential flow filtration (SPTFF) processes provide several advantages over recirculating, or traditional batch TFF processes, including simplicity, ease of use, and a smaller footprint, while avoiding some of the undesirable effects associated with recirculation, such as lower conversion.

SPTFF processes are typically performed at lower feed flow rates compared to traditional batch processes to facilitate conversion by increasing residence time within the module. The cassettes used in SPTFF processes are often processed in series, rather than in parallel, to improve conversion by increasing mass transfer through operation at higher feed flow rates. Although processing the cassettes in series can improve SPTFF performance and product recovery, parallel processing is often preferred for flushing SPTFF assemblies with liquids to remove preservative or storage solution, measure permeability, equilibrate the membranes, clean the membranes, or prepare the membranes for storage, particularly because serial processing requires additional time and material (e.g., water, buffer, cleaning solutions, storage solutions), which increases the overall cost of operation compared to parallel processing.

Since serial staging is desirable for product (e.g., protein) processing and parallel staging is desirable for flushing and cleaning SPTFF assemblies, there is a present need for SPTFF systems that can readily transition from processing cassettes in series to processing cassettes in parallel, and vice versa, while maintaining a sanitary processing environment.

In addition, current SPTFF systems suffer from a number of drawbacks, including lack of disposability for single-use operation, insufficient scalability (e.g., for linear scale-up or scale-down) and inadequate cleaning and product recovery methods.

Accordingly, there is a need for improved SPTFF assemblies that are scalable and/or disposable, as well as a need for more effective methods for cleaning and recovering target products (e.g., proteins) from the filtration membranes in TFF cassettes.

SUMMARY OF THE INVENTION

The present invention provides, in one embodiment, a single-pass tangential flow filtration (SPTFF) assembly, comprising a plurality of processing units that are fluidly connected, wherein each processing unit comprises a cassette holder containing at least one TFF cassette, and wherein the processing units in the assembly are configured for processing in parallel and/or in series; a first channel connected to a feed inlet extending through the plurality of processing units; a second channel connected to a retentate outlet extending through the plurality of processing units; a permeate channel extending through the plurality of processing units; and one or more valves, wherein each valve is located on either the first channel or the second channel between two adjacent processing units and wherein the valves alternate between the first channel and second channel for consecutive pairs of adjacent processing units. When the valves on the first and second channels are open, the processing units in the SPTFF assembly are processed in parallel. When the valves on the first and second channels are closed, the processing units in the SPTFF assembly are processed in series. In a particular embodiment, the valves in the SPTFF assembly are sanitary valves.

In another embodiment, the invention relates to a disposable single-pass tangential flow filtration (SPTFF) assembly, comprising one or more disposable components, wherein fluid contact surfaces on the disposable components are contained in a sealed disposable container that comprises tubing for making aseptic connections to feed and product vessels. The disposable components can include, for example, a disposable feed line, at least one disposable TFF cassette, a disposable holder for at least one TFF cassette, a disposable retentate line, and a disposable retentate valve, or a combination thereof.

In a further embodiment, the invention relates to a process for recovering proteins from the surface of a filtration membrane in a single-pass tangential flow filtration (SPTFF) assembly, comprising introducing a liquid feed comprising proteins into a feed channel in a SPTFF assembly; passing the liquid feed across a filtration membrane along the feed channel, thereby separating the liquid feed into a retentate and a permeate; stopping the flow of the liquid feed across the membrane for a period of time sufficient to allow permeate to diffuse through the membrane by osmosis, thereby displacing proteins from the surface of the membrane into the feed channel; and recovering the displaced proteins from the feed channel.

In an additional embodiment, the invention relates to a process for cleaning a tangential flow filtration (TFF) assembly, comprising flushing a liquid that lacks cleaning agent (e.g., water, buffer) through a feed channel in the TFF assembly for a period of time sufficient to allow the liquid to displace product from the surfaces of filtration membranes in the assembly to the feed channel; flushing the feed channel in the assembly with a cleaning solution comprising a cleaning agent, thereby removing the displaced product form the feed channel; stopping the flow of liquid through the assembly for a period of time sufficient to allow the cleaning agent to reach the internal surfaces of the assembly and diffuse into fouling deposits on the filtration membrane, thereby dissolving the fouling deposits; and flushing the assembly with a liquid that lacks the cleaning agent to remove residual cleaning agent from the assembly. In a particular embodiment, the process further comprises testing the assembly to determine whether the surface of the filtration membrane(s) has been restored to a desired level of cleanliness. Preferably, the TFF assembly is a SPTFF assembly.

In yet another embodiment, the invention relates to a method of increasing the processing capacity of a single-pass tangential flow filtration (SPTFF) assembly, comprising increasing the filtration membrane area in a SPTFF assembly; and increasing the volume of feed solution that is being delivered to the SPTFF assembly to a level that is proportional to the increase in filtration membrane area, wherein the residence time of the feed solution and length of the flowpath in the SPTFF assembly are maintained.

In a further embodiment, the invention relates to a method of adding a processing unit to a single-pass tangential flow filtration (SPTFF) assembly (e.g., for increasing processing capacity of the assembly). The method comprises establishing a fluid connection between a first processing unit in the SPTFF assembly and a second processing unit that is to be added to the SPTFF assembly, wherein the first and second processing units each comprise a cassette holder containing at least one TFF cassette, and wherein the first and second processing units are fluidly connected to each other by a first channel connected to a feed inlet, a second channel connected to a retentate outlet and a permeate channel. In accordance with the invention, a mechanical seal is positioned on the first channel between the first and second processing units, thereby preventing feed in the first channel in the first processing unit from flowing directly into the second processing unit and ensuring that the first and second processing units are processed in series. In a particular embodiment, the mechanical seal is a gasket.

In yet another embodiment, the invention relates to an adaptable modular single-pass tangential flow filtration (SPTFF) assembly comprising at least one processing unit that comprises a cassette holder containing at least one TFF cassette; a first channel connected to a feed inlet; a second channel connected to a retentate outlet; a permeate channel; and one or more valves, mechanical seals, or a combination thereof, between adjacent processing units in the assembly, thereby ensuring that the processing units in the assembly can be processed in series. In accordance with the invention, the at least one processing unit in the assembly can be fluidly connected to one or more additional processing units, and can accommodate one or more additional TFF cassettes having the same, or a different, filtration membrane area. In addition, the at least one TFF cassette in each processing unit can be replaced with one or more TFF cassettes having a different filtration membrane area.

The systems and processes described herein are suitable for single pass TFF applications, traditional batch (i.e., recirculating) TFF applications and partial recirculation TFF applications operated in single-pass mode where the permeate and a portion of the retentate from the system are recovered in separate containers without recirculation through the TFF system, and the remainder of the retentate is recirculated through the TFF system at least once. The retentate that is being recirculated can be returned to any upstream location in or before the TFF system, for example the retentate is recirculated to the feed tank or to the feed line near the feed pump before the feed inlet on the TFF system.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Definitions

Figure 1:
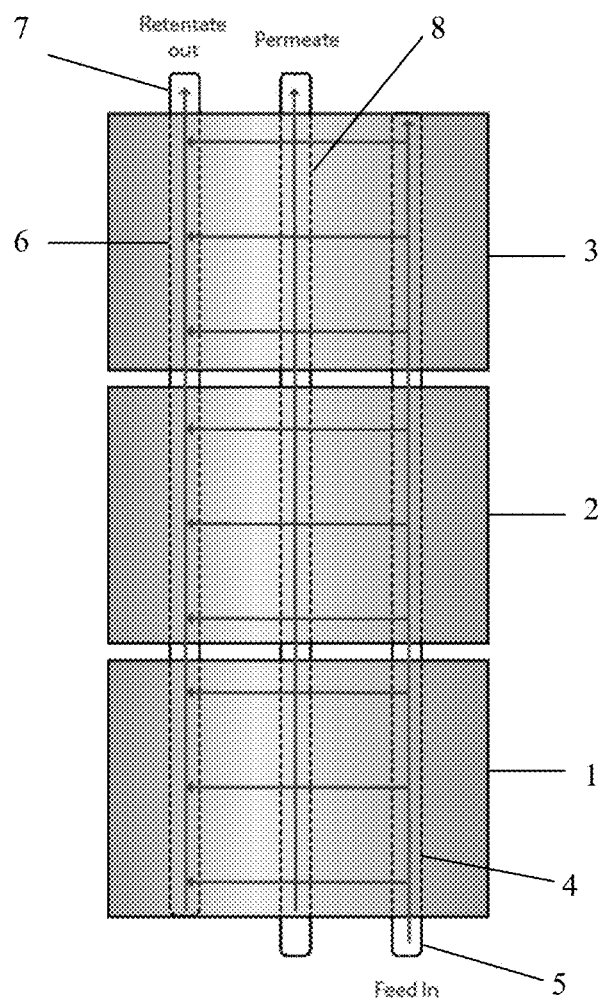
FIG. 1 is a diagram depicting a standard TFF system with three processing units that are operated in parallel.

Unless defined otherwise, all technical and scientific terms used herein have the same meaning as commonly understood by one of ordinary skill in the art to which this invention pertains.

"SPTFF assembly," "SPTFF system" and "SPTFF apparatus" are used interchangeably herein to refer to a TFF system that is configured for operation in a single-pass TFF mode.

"Single-pass TFF mode" refers to operating conditions for a TFF system/assembly under which all or a portion of the retentate is not recirculated through the system.

The terms "feed," "feed sample" and "feed stream" refer to the solution being fed to the filtration module for separation.

The term "separation" generally refers to the act of separating the feed sample into two streams, a permeate stream and a retentate stream.

The terms "permeate" and "permeate stream" refer to that portion of the feed that has permeated through the membrane.

The terms "retentate" and "retentate stream" refer to the portion of the solution that has been retained by the membrane, and the retentate is the stream enriched in a retained species.

"Feed line" or "feed channel" refers to a conduit for conveying a feed from a feed source (e.g., a feed container) to one or more processing units in a filtration assembly (e.g., an SPTFF assembly).

"Retentate line" or "retentate channel" refers to a conduit in a filtration assembly for a retentate or retentate stream.

"Permeate line" or "permeate channel" refers to a conduit in a filtration assembly for a permeate or permeate stream.

The expression "flow path" refers to a channel comprising a filtration membrane (e.g., ultrafiltration membrane, microfiltration membrane) through which the solution being filtered passes in a tangential flow mode. The flow path can have any topology which supports tangential flow (e.g., straight, coiled, arranged in zigzag fashion). A flow path can be open, as in an example of channels formed by hollow fiber membranes, or have one or more flow obstructions, as in the case, for example, of rectangular channels formed by flat-sheet membranes spaced apart by woven or non-woven spacers.

A "processing unit" or "unit" refers to a cassette holder comprising one or more cassettes.

A "cassette holder" refers to a container for one or more cassettes. Typically, when a cassette holder contains more than one cassette, the cassettes are configured for parallel processing, although, in some embodiments, the cassettes can be configured for serial processing.

A "cassette" refers to a cartridge or plate-and-frame structure comprising a filtration membrane (e.g., an ultrafiltration membrane, a microfiltration membrane) suitable for TFF processes.

"Filtration membrane" refers to a selectively permeable membrane for separating a feed into a permeate stream and a retentate stream using a TFF process. Filtration membranes include, but are not limited to, ultrafiltration (UF) membranes, microfiltration (MF) membranes, reverse osmosis (RO) membranes and nanofiltration (NOF) membranes.

The terms "ultrafiltration membrane" and "UF membrane" are used herein to refer to a membrane that has pore sizes in the range of between about 1 nanometer to about 100 nanometers.

The term "microfiltration membranes" and "MF membranes" are used herein to refer to membranes that have pore sizes in the range between about 0.1 micrometers to about 10 micrometers.

The term "plurality," when used herein to describe processing units, refers to two or more (e.g., two, three, four, five, etc.) processing units.

"Fluidly connected" refers to a plurality of processing units that are connected to one another by one or more conduits for a liquid, such as, for example, a feed channel, retentate channel and/or permeate channel.

"Product" refers to a target compound in a feed. Typically, a product will be a biomolecule (e.g., protein) of interest, such as a monoclonal antibody (mAb).

"Processing" refers to the act of filtering (e.g., by SPTFF) a feed containing a product of interest and subsequently recovering the product in a concentrated form. The concentrated product can be recovered from the filtration system (e.g., a SPTFF assembly) in either the retentate stream or permeate stream depending on the product's size and the pore size of the filtration membrane.

The expressions "parallel processing", "processing in parallel", "parallel operation" and "operation in parallel" refer to processing a product in a TFF assembly (e.g., SPTFF assembly) that contains a plurality of processing units that are fluidly connected by distributing the feed directly from the feed channel to each of the processing units in the assembly.

The expressions "serial processing", "processing in series", "serial operation" and "operation in series" refer to processing a product in a TFF assembly (e.g., SPTFF assembly) that contains a plurality of processing units that are fluidly connected by distributing the feed directly from the feed channel to only the first processing unit in the assembly. In serial processing, each of the other, subsequent processing units in the assembly receives its feed from the retentate line of the preceding processing unit (e.g., the retentate from a first processing unit serves as the feed for a second, adjacent processing unit).

The expressions "conversion," "single-pass conversion," and "conversion per pass" are used herein to denote the fraction of the feed volume that permeates through the membrane in a single pass through the flow channels, expressed as a percentage of the feed stream volume. The term "residence time" refers to holdup volume divided by flow rate.

Single-Pass Tangential Flow Filtration (TFF) Systems

Tangential flow filtration (TFF) is a separation process that uses membranes to separate components in a liquid solution or suspension on the basis of size, molecular weight or other differences. In traditional TFF processes, the fluid is pumped tangentially along the membrane surface and particles or molecules which are too large to pass through the membrane are rejected and returned to a process tank for additional passes across the membrane (i.e., recirculation) until the process fluid is sufficiently clarified, concentrated or purified. The cross-flow nature of TFF minimizes membrane fouling, thus permitting high volume processing per batch.

Traditional batch-fed recirculation TFF processes, however, are limited due to the size and minimum working volume of existing TFF systems. Single-Pass TFF (SPTFF) allows direct flow-through concentration of a product (e.g., protein) in the absence of recirculation, which reduces overall system size through elimination of mechanical components and permits continuous operation at high conversion levels. While existing SPTFF systems and processes provide several advantages over traditional recirculating TFF systems and processes, there is a need for improved SPTFF systems and processes that provide users with added operating flexibility, reduced processing time and buffer requirements, and increased product yield and recovery.

In general, the SPTFF systems/assemblies described herein (also referred to as SPTFF systems/assemblies of the invention) can be assembled and operated using standard, existing TFF system components that are well known and are commercially available. Standard TFF system components that are commercially available generally include, for example, TFF cassettes comprising filtration membranes, cassette holders, conduits (e.g., tubing, piping) for feed, retentate and permeate, a housing or enclosure, valves, gaskets, a pump module (e.g., pump module comprising a pump housing, diaphragm and check valve) one or more reservoirs (e.g., bioprocess containers) and a pressure gauge.

Exemplary cassettes (e.g., TFF cassettes) that are suitable for use in the SPTFF systems of the invention include, but are not limited to, TFF cassettes supplied by EMD Millipore Corporation (Billerica, Mass.), such as, for example, Pellicon® cassettes with Biomax™ membrane or Ultracel™ membrane (e.g., Pellicon® XL 50 cassettes, Pellicon® 2 cassettes, Pellicon® 2 Mini cassettes, Pellicon® 2 Maxi cassettes, Pellicon® 3 cassettes), Prostak™ microfiltration modules, and Prep/Scale® TFF cartridges). Additional TFF cassettes capable of being used in SPTFF systems include, e.g., T-series cassettes with Delta membrane for Cadence™ SPTFF modules (Pall Corporation, Port Washington, N.Y.), Kvick™ Flow cassettes (GE Healthcare Bio-Sciences, Piscataway, N.J.) and Hydrosart® cassettes (Sartorius AG, Bohemia, N.Y.).

Cassette holders that are suitable for use in SPTFF assemblies include, for example, Pellicon® cassette holders (EMD Millipore Corporation, Billerica, Mass.) such as, for example, Pellicon® 2 miniholders, acrylic Pellicon® holders, stainless steel Pellicon® holders, process scale Pellicon® holders. Other suitable cassette holders include, but are not limited to, Centramate™ TFF membrane cassette holders, Centrasette™ TFF membrane cassette holders, Maximate™ TFF membrane cassette holders and Maxisette™ TFF membrane cassette holders (Pall Corporation, Port Washington, N.Y.). In some embodiments, existing cassette holders (e.g., Pellicon® cassette holders (EMD Millipore Corporation)) can be modified to function in the hybrid, disposable, scalable and/or adapatable SPTFF assemblies described herein.

In various embodiments, the SPTFF system components can be disposable. Exemplary disposable components for SPTFF assemblies include, but are not limited to, components of Flexware® assemblies for Mobius® FlexReady Solution for TFF (EMD Millipore Corporation, Billerica, Mass.). Other disposable components for SPTFF assemblies include, for example, components of Allegro™ TFF assemblies (Pall Corporation, Port Washington, N.Y.).

Hybrid SPTFF Systems

For biotechnology applications, ultrafiltration (UF) cassettes are typically run in a batch process where the retentate is returned to a retentate tank and circulated through the cassette multiple times. Single-pass TFF (SPTFF) allows continuous processing but can require more membrane area. It has advantages in niche applications such as de-watering (concentration) to debottleneck tanks or increase column utilization, achieve higher final concentrations, and buffer condition fluids before columns. For achieving higher final concentrations, SPTFF avoids constraints on batch systems such as system footprint, a minimum working volume or dilution during product recovery.

TFF systems operated in parallel typically have processing units (e.g., cassette holders containing TFF cassettes) that are stacked vertically. The vertical stack of process holders typically shares a feed line, a retentate line, and a permeate line in common for parallel operation (see FIG. 1). However, optimized implementation of an SPTFF assembly utilizes processing units that are operated in series such that the retentate from a processing unit serves as feed for the subsequent adjacent processing unit.

Since serial operation is advantageous for product (e.g., protein) processing and recovery, and parallel operation is desirable for flushing and cleaning TFF assemblies, the present invention contemplates a TFF system (e.g., a SPTFF system) that is configured for processing in series and in parallel, referred to herein as a "hybrid system" or "hybrid assembly." The hybrid system can be operated in parallel for particular processes (e.g., flushing, equilibration, cleaning, preparation for storage, measurement of NWP), or in series for product processing and recovery.

Accordingly, in one embodiment, the invention provides a tangential flow filtration (TFF) assembly (e.g., a single-pass tangential flow filtration (SPTFF) assembly), comprising a plurality of processing units that are fluidly connected, wherein each processing unit comprises a cassette holder containing at least one TFF cassette, and wherein the processing units in the assembly are configured for processing in parallel and/or in series; a first channel connected to a feed inlet extending through the plurality of processing units; a second channel connected to a retentate outlet extending through the plurality of processing units; a permeate channel extending through the plurality of processing units; and one or more valves located on either the first channel or the second channel between two adjacent processing units. According to this aspect of the invention, the valves alternate between the first channel and second channel for consecutive pairs of adjacent processing units, such that the plurality of processing units are processed in parallel when all of the valves are open (FIG. 2), or in series when all of the valves are closed (FIG. 3).

In one embodiment, the valves are built into the cassette holder of each processing unit. In another embodiment, the valve is separate from the cassette holder. Preferably, the valves are sanitary valves. As used herein, a "sanitary valve" is a valve that can maintain a sterile connection regardless of whether the valve is open or closed. Typically, a sanitary valve will be compatible, non-toxic, sanitizeable and non-shedding.

A hybrid SPTFF system of the invention can have two or more stages. In one embodiment, a hybrid SPTFF assembly has only two processing units. When there are only two processing units, a single valve on the first channel between the two processing units can be used to toggle between serial and parallel processing. For example, the two processing units are operated in parallel when the valve on the first channel is open, and operated in series when the valve is closed.

Preferably, hybrid SPTFF assemblies of the invention include three or more (e.g., four, five, six, seven, eight) processing units. The processing units can be stacked (e.g., stacked vertically) to form a stacked assembly.

When there are three or more processing units, the valves on the first channel alternate with valves on the second channel between consecutive pairs of adjacent processing units (e.g., a series of three processing units, wherein the first and second processing units in the series constitutes a first pair of adjacent processing units, and the second and third processing units in the series constitutes a second pair of adjacent processing units, wherein the first and second pairs of processing units are ordered consecutively in the series). For example, a hybrid SPTFF assembly having three processing units preferably has a valve positioned on the first channel between the first and second processing units in the series, while a second valve is positioned on the second channel between the second and third processing units in the series (see, e.g., FIGS. 2 and 3). In another example, a hybrid SPTFF assembly having a series of five processing units has valves on the first channel between the first and second processing units and between the third and fourth processing units in the series, while valves are positioned on the second channel between the second and third processing units and the fourth and fifth processing units in the series.

FIG. 1 depicts a valve-less SPTFF assembly having three processing units 1, 2, 3 that are fluidly connected, a first channel 4 extending from a feed inlet 5 through each of the processing units 1, 2, 3, a second channel 6 that extends through the processing units 1, 2, 3 and is connected to a retentate outlet 7, and a permeate channel 8 extending through the processing units 1, 2, 3. Vertical arrows show the direction of the flowpaths for the feed, retentate and permeate, while horizontal arrows show the direction of the flowpath through the processing units. In the absence of valves on the first and second channels, the feed is distributed in a parallel fashion to all three of the processing units through the first channel, while retentate from each of the processing units flows through the second channel and out of the assembly through the retentate outlet.

Figure 2:
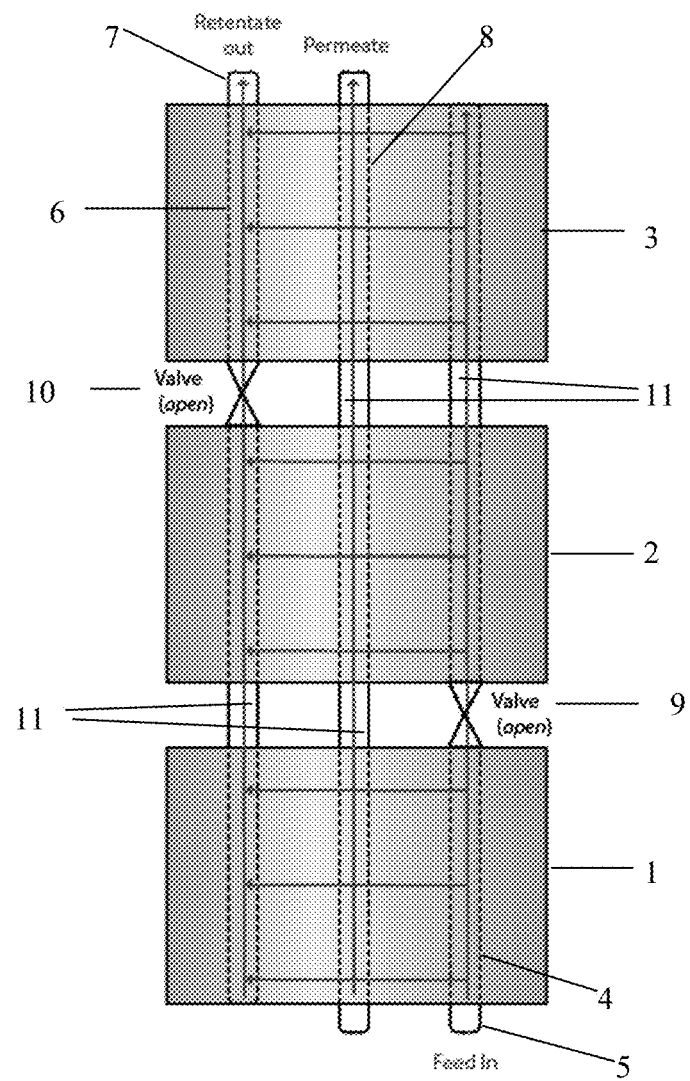
FIG. 2 is a diagram depicting a TFF system of the invention having three processing units that can be operated in parallel or in series, showing open valves for operation in parallel.
Figure 3:
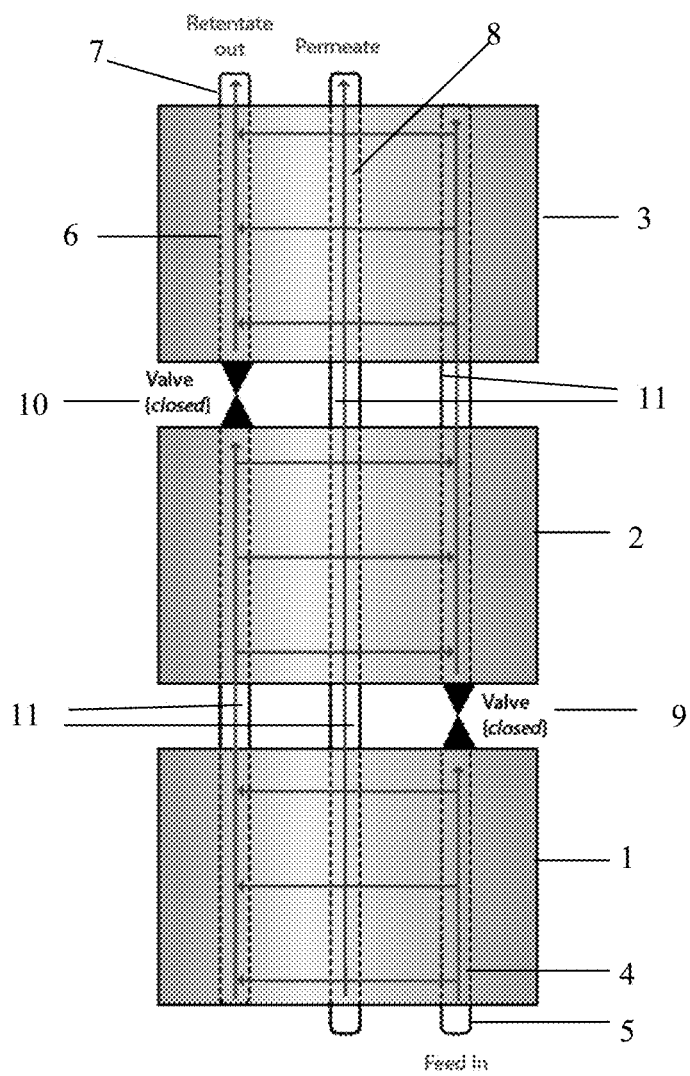
FIG. 3 is a diagram depicting a TFF system of the invention having three processing units that can be operated in parallel or in series, showing closed valves for operation in series.

FIGS. 2 and 3 depict a similar SPTFF assembly having three processing units 1, 2, and 3 that are fluidly connected, except that the assemblies in FIGS. 2 and 3 each contain a valve 9 on the first channel between adjacent processing units 1, 2, and a valve 10 on the second channel between a subsequent consecutive pair of adjacent processing units 2, 3. Valve-less spool pieces 11 are located on the second channel 6 and permeate channel 8 between processing units 1 and 2, and on the first channel 4 and permeate channel 8 between processing units 2 and 3. In FIG. 2, the valve 9 on the first channel and valve 10 on the second channel are both open to allow for parallel processing of the processing units 1, 2, 3 (e.g., for flushing or cleaning the assembly). In contrast, the valve 9 on the first channel and valve 10 on the second channel in FIG. 3 are both closed to allow for serial processing of the three processing units 1, 2, 3 (e.g., for product processing and recovery).

Figure 4:
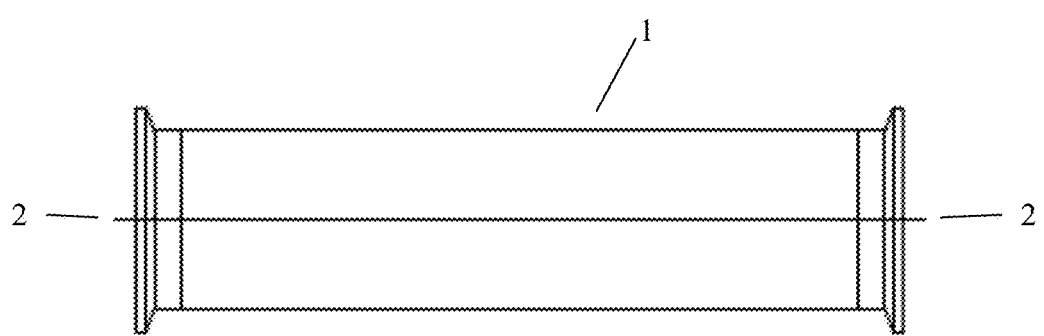
FIG. 4 is a diagram of a spool piece for a hybrid SPTFF assembly of the invention.

In some embodiments, each valve in the hybrid assembly has a corresponding spool piece located on a different channel between the same processing units. In general, the spool piece is an open conduit with sanitary ends that connects the retentate channel from one process holder to the feed channel of the following process holder, or connects the permeates channels of adjacent process holders. Preferably, the length of the spool piece is chosen to match that of the sanitary valve so the assembly has a balanced height. An exemplary spool piece for a hybrid SPTFF assembly described herein is depicted in FIG. 4. The spool piece in FIG. 4 includes an open cylindrical body 1 capable of acting as a fluid conduit with flanges 2 located at both ends. In some embodiments, the hybrid assembly can have a valve on the first channel and a spool piece on the second channel between the first and second processing units in a series of two processing units. Alternatively, or additionally, the assembly can have a spool piece on the first channel and a valve on the second channel between the same two adjacent processing units. For example, in a hybrid SPTFF assembly having three processing units, there can be a valve on the first channel and a spool piece on the second channel between the first and second processing units, and a valve on the second channel and a spool piece on the first channel between the second and third processing units (see, e.g., FIGS. 2 and 3).

Preferably, the hybrid SPTFF assembly is in a container (e.g., housing) that shields the assembly and its components from the external environment. For example, the assembly (e.g., stacked assembly) can be inserted into a rigid container that applies a compressive force to seal the assembly from the external environment. The disposable container (e.g., a rigid holder) can include tubing (e.g., disposable tubing) at each end for making connections (e.g., aseptic connections) to feed and product containers (e.g., vessels, bags), respectively, such that an operator of the hybrid assembly can toggle between serial and parallel operation without opening the system to the outside environment and/or removing devices from the holders.

Disposable SPTFF Systems

Traditionally, a TFF process involves time consuming and costly validation of both TFF system and cassette cleaning. The use of disposable components would eliminate the need for membrane and system cleaning as well as mitigate risk of product carryover from one batch to the next. These assemblies are a complete, self-contained TFF flow path consisting of a process container, tubing, connectors, and disposable cassette manifolds that eliminate fluid contact from any reusable components. Using disposable components in TFF processing provides many benefits without sacrificing robust manufacturing processes.

SPTFF assemblies have the advantages of simplicity (e.g., no tank, no retentate recycle, no control skid) and ease of use over conventional batch TFF apparatuses. The simplicity and ease-of-use features of SPTFF assemblies can be improved by making single-use, disposable SPTFF assemblies that can facilitate plug-and-play installation and easy disassembly of flowpath components, and require no cleaning or sanitization between operations.

Thus, in another embodiment, the invention relates to a disposable single-pass tangential flow filtration (SPTFF) assembly, comprising one or more disposable components, wherein fluid contact surfaces on the disposable components are contained (e.g., enclosed) in a disposable container (e.g., a sealed disposable container). Preferably, the disposable container (e.g., a rigid holder) includes tubing (e.g., disposable tubing) at each end for making connections (e.g., aseptic connections) to feed and product containers (e.g., vessels, bags), respectively.

Typically, a disposable SPTFF assembly of the invention includes a disposable feed line, a disposable TFF cassette, a disposable TFF cassette holder, a disposable retentate line, and a disposable retentate valve, or a combination thereof.

Figure 5:
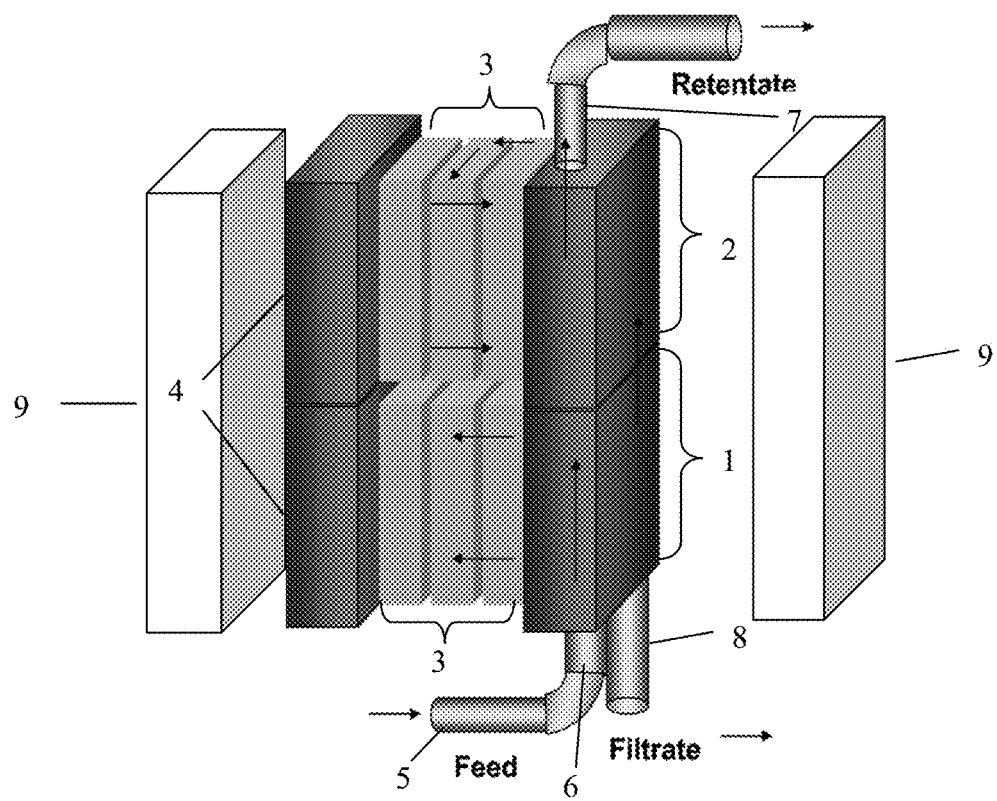
FIG. 5 is a diagram depicting a disposable SPTFF assembly having two processing units.

The disposable components and container are made from disposable materials (e.g., plastic, rubber, metal). Preferably, the disposable components and container are made from plastic. An exemplary disposable SPTFF assembly of the invention is depicted in FIG. 5. The disposable SPTFF assembly in FIG. 5 has two processing units 1, 2. Horizontal arrows indicate the flow direction of the feed liquid through the disposable TFF cassettes 3 in each processing unit while vertical arrows show the direction of the flowpath between the processing units 1, 2. Disposable liners 4 are positioned adjacent to the disposable TFF cassettes 3. Other components shown include a disposable feed inlet 5 connected to a disposable feed channel 6, a disposable retentate outlet 7, a disposable permeate outlet 8 and disposable holder plates 9.

Disposable SPTFF assembly components are well known and are available commercially. Exemplary disposable components for SPTFF assemblies include, but are not limited to, components of Flexware® assemblies for Mobius® FlexReady Solution for TFF (EMD Millipore Corporation, Billerica, Mass.). Other disposable components for SPTFF assemblies include, for example, components of Allegro™ TFF assemblies (Pall Corporation, Port Washington, N.Y.).

Typically, the disposable feed and retentate lines are made from disposable tubing. In one embodiment, the disposable retentate line further comprises a T line (e.g., a disposable T line) for in-line buffer addition (e.g., for a diafiltration-type mode of operation).

In one embodiment, the disposable SPTFF assembly includes a disposable retentate valve that is a pinch valve (e.g., diaphragm valve) for disposable tubing. The pinch valve can be disposable or removable/re-useable. Preferably, the valve is low shear and sanitary (e.g., compatible, non-toxic, sanitizeable, non-shedding).

In certain embodiments, the disposable SPTFF assembly further comprises a disposable pressure sensor. In other embodiments, the disposable SPTFF assembly comprises a disposable diaphragm for a pressure sensor, through which pressure is monitored with a reusable sensor.

In a particular embodiment, the disposable SPTFF assembly comprises a plurality of processing units that are fluidly connected, wherein each processing unit comprises at least one TFF cassette in a cassette holder. In a further embodiment, the plurality of processing units are stacked (e.g., stacked vertically) to produce a stacked assembly. For example, the processing units can be stacked for use with diverter plates (e.g., separator plates for Pellicon® 2 Mini Holders (EMD Millipore, Billerica, Mass.)). The stacked assembly can be inserted into a rigid container that would apply a compressive force to seal the assembly from the external environment and prevent bypass flow from the membrane upstream (feed/retentate) side to the membrane downstream (permeate) side, thereby producing a sealed disposable container.

The disposable SPTFF assembly can also comprise one or more disposable end plates (e.g., disposable retentate end plates). For example, larger-sized disposable SPTFF assemblies (e.g., assemblies having a filtration area greater than 5 $m^2$) can include a disposable feed end plate and a disposable retentate end plate that would bypass the process holder but still allow the compressive force in the holder to work and seal the cassettes.

In some embodiments, one or more of the disposable components in the disposable SPTFF assembly can be replaceable (e.g., capable of plug-and-play installation and disassembly).

Preferably, the disposable SPTFF assembly is sanitized (e.g., sterilized) prior to use in a SPTFF process. Suitable methods for sanitizing SPTFF assemblies can readily be determined by persons of ordinary skill in the art based on compatibility of the sanitization method with the material(s) in the assembly. Exemplary sanitization methods include treatment of the assembly with a suitable sanitization agent such as, for example, gamma radiation, ethylene oxide (ETO), bleach (e.g., Clorox), chlorine (e.g., NaOCl), peroxide, acid (e.g., peracetic acid), base (e.g., NaOH), formaldehyde (e.g., formaline solution) or heat, or an appropriate combination thereof.

Installation of a disposable SPTFF assembly typically involves establishing aseptic connections between the disposable SPTFF assembly and feed and product containers at opposing ends. For example, the disposable tubing of the feed line for the SPTFF assembly can be connected to a feed container and the disposable tubing of the retentate line for the SPTFF assembly can be connected to a product container.

Accordingly, in another embodiment, the invention relates to a method of installing a disposable single-pass tangential flow filtration (SPTFF) assembly, comprising establishing a first aseptic connection between a feed line of a disposable SPTFF assembly and a feed container, and establishing a second aseptic connection between a retentate line of the disposable SPTFF assembly and a product container.

Scalable SPTFF Assemblies and Processes

Small scale SPTFF systems are typically used for testing and analysis while large scale SPTFF systems are commonly used in manufacturing operations. There is an existing need for scalable systems that can transition between small scale testing and large scale manufacturing. Such scalable systems preferably can be operated using existing, commercially available components without the need for system redesign.

Linear scaling represents one means of achieving the scaling-up or scaling-down of SPTFF assemblies while ensuring that the performance between the larger and smaller scales is comparable (see, for example, van Reis, et al., "Linear Scale Ultrafiltration," *Biotechnology and Bioengineering* 55(5): 737-746 (1997), the contents of which are incorporated herein by reference). As used herein, "scaling-up" refers to increasing the processing capacity of a SPTFF assembly while maintaining both the residence time of the sample and the length of the flowpath, and "scaling-down" refers to decreasing the processing capacity of a SPTFF assembly while maintaining both the residence time of the sample and the length of the flowpath (e.g., for process development and trouble-shooting purposes).

Thus, in one embodiment, the invention relates to a method of increasing the processing capacity of a single-pass tangential flow filtration (SPTFF) assembly, comprising the steps of increasing the filtration membrane area in a SPTFF assembly; and increasing the volume of feed solution that is being delivered to the SPTFF assembly by an amount that is proportional to the increase in filtration membrane area (e.g., by increasing the volumetric flow). The volumetric flow can be increased, for example, using a pump or vacuum to apply pressure, or using gravity. According to this aspect of the invention, both the residence time of the feed solution in the SPTFF assembly and the length of the flowpath are maintained.

The filtration membrane area can be increased while maintaining the length of the flowpath by replacing one or more cassettes in the assembly with an equal number of cassettes having a greater filtration membrane area, by adding additional cassettes to the assembly, or a combination of the two. For example, one or more cassettes (e.g., minicassettes) having an effective filtration area of, e.g., 0.05 $m^2$ or 0.1 $m^2$ in a small scale SPTFF assembly can be replaced by an equal number of larger TFF cassettes having an effective filtration area of, e.g., 1.0 $m^2$ or 2.5 $m^2$ to increase the overall filtration area in the assembly. Typically, up to about 10 $m^2$ of effective filtration area can be attained on each side of the manifold segment in a processing unit. The effective filtration area can be added in parallel or in series.

Figure 6:
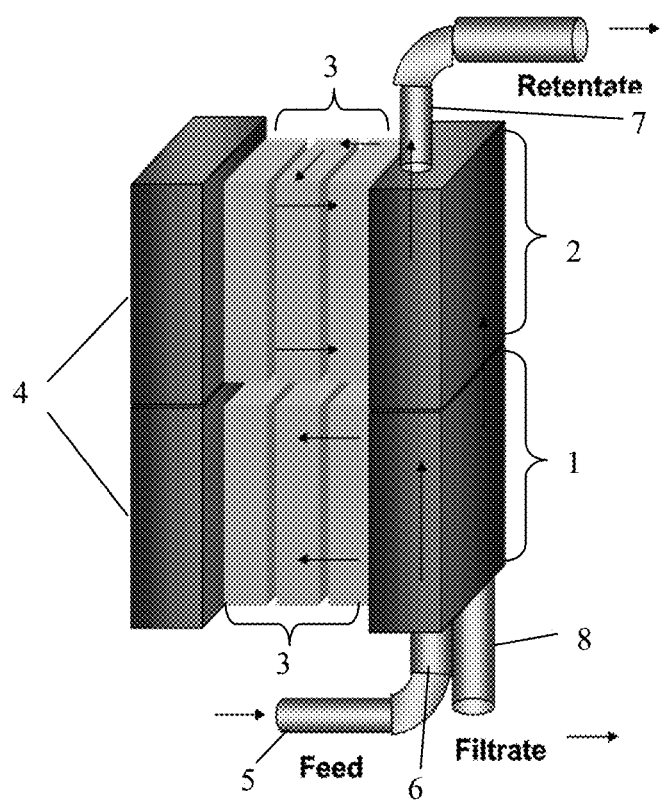
FIG. 6 is a diagram depicting a scalable SPTFF assembly having two processing units.

FIG. 6 depicts a scalable SPTFF assembly having two processing units 1, 2, each processing unit having three TFF cassettes 3. Scaling of the assembly can be achieved without altering the flowpath length through processing units 1, 2 by replacing one or more of the TFF cassettes 3 in each processing unit with an equal number of TFF cassettes having a greater (for scaling up) or lesser (for scaling down) filtration membrane area. Alternatively, scaling of the assembly can be achieved without altering the flowpath length by adding or subtracting TFF cassettes (e.g., TFF cassettes having the same effective filtration area) to or from each processing unit, such that each processing unit will contain from 1 to about 10 TFF cassettes.

SPTFF Assemblies Comprising Mechanical Seals for Serial Processing

Serial processing of a SPTFF system can also be achieved using a mechanical seal (e.g., a rigid plate, a flexible gasket) that is positioned on the channel that serves as the feed line between two adjacent processing units that are processed in parallel. According to this aspect of the invention, the mechanical seal can prevent feed flow from distributing to adjacent processing units, enabling the retentate from the first processing unit to flow to the subsequent adjacent processing unit as its feed. As a result, the two processing units are processed in series.

Figure 7:
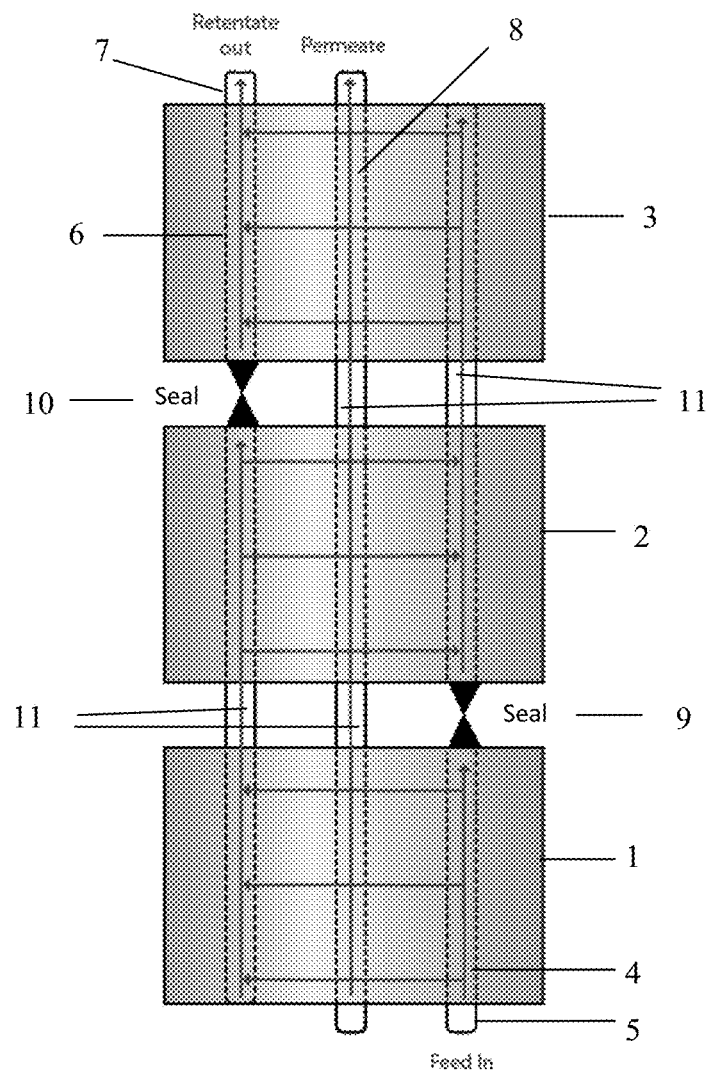
FIG. 7 is a diagram depicting a TFF system of the invention having three processing units and showing seals between adjacent processing units for operation in series.

FIG. 7 depicts a SPTFF assembly having three processing units 1, 2, and 3 that are fluidly connected. A first seal 9 is positioned on the first channel 4 that is connected to the feed inlet 5 between adjacent processing units 1, 2, and a second seal 10 is positioned on the second channel 6 between a subsequent consecutive pair of adjacent processing units 2, 3 to allow for serial processing of the three processing units 1, 2, 3 (e.g., for product processing and recovery). Spool pieces 11 are positioned on the second channel 6 and permeate channel 8 between processing units 1 and 2, and on the first channel 4 and permeate channel 8 between processing units 2 and 3. In the absence of the seals, filtrate (permeate) can pass directly from one processing unit to the other. In contrast, when the seals are present, feed is prevented from flowing directly from the first processing unit 1 to the second processing unit 2. Accordingly, retentate from the first processing unit 1 serves as the feed for the second processing unit 2, thereby ensuring serial processing.

Accordingly, in another embodiment, the invention relates to a method of adding a processing unit to a single-pass tangential flow filtration (SPTFF) assembly. The method comprises establishing a fluid connection between a first processing unit in the SPTFF assembly (e.g., a processing unit in the assembly that is connected to a retentate outlet) and a second processing unit that is to be added to the SPTFF assembly (e.g., an isolated processing unit or a first processing unit in a series of two or more processing units to be added to the assembly). The first and second processing units each contain a cassette holder containing at least one TFF cassette and are fluidly connected to each other by one or more fluid channels. Preferably, the first and second processing units are fluidly connected by a first channel connected to a feed inlet, a second channel connected to a retentate outlet and a permeate channel.

The method further involves the step of positioning a mechanical seal on the first channel between the first and second processing units, thereby preventing feed in the first channel in the first processing unit from flowing directly into the second processing unit and ensuring that the first and second processing units are processed in series (FIG. 7). For example, the mechanical seal can be positioned (e.g., inserted, included) between the flanges of two connected cylinders forming part of the feed channel of a SPTFF assembly between two adjacent processing units.

Suitable mechanical seals for use in a SPTFF assembly of the invention are well known. In one embodiment, the mechanical seal is a gasket, such as, for example, a gasket that closes off an opening or a gasket having a length sufficient to closes off any dead volume between the opening and a first passage in a manifold. Preferably, the gasket is flexible and sanitary (e.g., a gasket that is non-shedding, cleanable, sanitizable, and has low extractables). The gasket can include an elastomeric material or metal (e.g., a metal foil). An exemplary gasket for a SPTFF assembly according to this aspect of the invention is part# A84MP-G from Newman Gasket Co., Lebanon, Ohio.

Adaptable Modular Single-Pass Tangential Flow Filtration (SPTFF) Systems

In other embodiments, the invention relates to an adaptable modular single-pass tangential flow filtration (SPTFF) assembly. Typically, the adaptable modular assembly comprises at least one processing unit that comprises a cassette holder containing at least one TFF cassette; a first channel connected to a feed inlet; a second channel connected to a retentate outlet; a permeate channel; and one or more valves, mechanical seals, or a combination thereof, between adjacent processing units in the assembly, thereby ensuring that the processing units in the assembly can be processed in series.

As used herein, "adaptable" means that the processing capacity of a modular assembly can be increased or decreased to achieve desired performance parameters, such as, but not limited to, a desired level of cleanliness of the assembly, enhanced target processing, and reduction of batch variability. The processing capacity of the adaptable assembly can be increased or decreased by, for example, adding or removing one or more processing units to or from the assembly. Alternatively, or in addition, the processing capacity of the adaptable assembly can be increased or decreased by adding or subtracting TFF cassettes from one or more processing units in the assembly, and/or by replacing one or more TFF cassettes in one or more processing units in the assembly with an equal number of TFF cassettes having a different membrane filtration area.

"Modular" refers to an adaptable assembly comprising one or more recurring components that can be added to, or removed from, the assembly to alter the processing capacity. Such recurring components include, for example, processing units and TFF cassettes.

In accordance with the invention, the at least one processing unit in the assembly can be fluidly connected to one or more additional processing units (e.g., by establishing an aseptic connection), as described herein. For example, about 1, 2, 3, 4, 5, 6, 7, etc., processing units can be added to an adaptable modular assembly already containing 1, 2, or 3 processing units.

In some embodiments, the processing unit can also accommodate one or more additional TFF cassettes. For example, about 1, 2, 3, 4, 5, 6, 7, etc., TFF cassettes can be added to a processing unit containing 1, 2, or 3 TFF cassettes. In one embodiment, the processing unit can accommodate up to about 10 TFF cassettes. The TFF cassettes being added can have the same, or a different, filtration membrane area as the TFF cassette(s) already present in the processing unit.

In further embodiments, the at least one TFF cassette in each processing unit can be replaced with one or more TFF cassettes having a different filtration membrane area. For example, if the TFF cassette in a processing unit has an effective filtration area of $0.1$ $m^2$, it can be replaced with a larger TFF cassettes having an effective filtration area of, e.g., $2.5$ $m^2$. The effective filtration area can be added in parallel or in series.

In one embodiment, the adaptable modular assembly comprises one or more valves between adjacent processing units, as described herein above for hybrid SPTFF systems of the invention. The presence of the valves ensures that the processing units in the adaptable assembly can be processed in series when the valves are closed, which can be advantageous for sample processing, or in parallel when the valves are open, which is useful for cleaning the assembly.

In an alternative embodiment, the adaptable modular assembly comprises one or more seals between adjacent processing units, as described herein above for SPTFF assemblies of the invention comprising mechanical seals. The presence of the seals ensures that the processing units in the adaptable assembly are processed in series, which is useful for sample processing applications.

The various embodiments described herein with regard to the hybrid, disposable and scalable SPTFF systems of the invention are equally applicable to the adaptable modular systems of the invention.

In another embodiment, the invention relates to a method of altering the processing capacity of an adaptable modular SPTFF assembly of the invention, comprising adding or removing at least one processing unit to or from the assembly;
replacing at least one TFF cassette in one or more processing units in the assembly with a TFF cassette having a different filtration membrane area; adding or removing at least one TFF cassette to or from one or more processing units in the assembly; or
a combination thereof.

Single-Pass Tangential Flow Filtration (SPTFF) Processes and Methods

The invention further relates to processes and methods for increasing product recovery from SPTFF systems and processes and methods for cleaning SPTFF assemblies (also referred to collectively as processes and methods of the invention).

SPTFF systems that are particularly suitable for use in the processes and methods described herein include, for example, the partial recirculation TFF, hybrid, disposable and scalable SPTFF systems/assemblies that are described herein above. Other TFF systems capable of being used in the processes and methods described herein are well known in the art to which the present invention pertains and include, but are not limited to, those described in U.S. Pat. No. 5,147,542, the contents of which are incorporated herein by reference in their entirety, and commercially available TFF systems from EMD Millipore Corporation (Billerica, Mass.) including, for example, Labscale™ TFF Systems, Cogent M1 TFF Systems, Cogent μScale TFF Systems, Flexware Assemblies for TFF, ProFlux TFF Systems, and Prostak TFF Systems. Other commercially available TFF Systems that can be operated in single pass mode include, e.g., Cadence™ Single Pass TFF Systems and Allegro™ TFF Systems (Pall Corporation, Port Washington, N.Y.).

Processes for Increasing Product Recovery from SPTFF Systems

General methods for recovering product (e.g., target proteins) from batch TFF systems typically use an initial recirculation through the system to depolarize proteins adsorbed to the filtration membranes and increased their recovery during a subsequent air blow-down or buffer flush of the cassette feed channel. For SPTFF assemblies, however, a recirculation step cannot be employed to depolarize proteins adsorbed to the filtration membranes without introducing a recirculation loop and taking away the simplicity and ease-of-use benefits of SPTFF.

The present invention contemplates, in one embodiment, processes for recovering proteins from the surface of a filtration membrane in a single-pass tangential flow filtration (SPTFF) assembly using a static hold recovery step. As used herein, a "static hold recovery step" refers to a step during which the pressurized flow of liquid through the SPTFF system is stopped to allow permeate in the system to flow backward through the filtration membranes by osmosis. According to this aspect of the invention, the backward flow of permeate through the membranes pushes proteins off the membrane surfaces and into the feed channel. The proteins removed from the membranes can subsequently be displaced from the feed channel, e.g., using a standard air blow-down or buffer flush.

Accordingly, the invention relates, in one embodiment, to a process for recovering proteins from the surface of a filtration membrane in a single-pass tangential flow filtration (SPTFF) assembly. The protein recovery process comprises the steps of introducing a liquid feed comprising proteins into a feed channel in a SPTFF assembly; passing the liquid feed across a filtration membrane along the feed channel, thereby separating the liquid feed into a retentate and a permeate; stopping the flow of the liquid feed across the membrane for a period of time sufficient to allow permeate to diffuse backwards through the membrane by osmosis, thereby displacing proteins from the surface of the membrane back into the feed channel; and recovering the displaced proteins from the feed channel.

The flow of liquid is stopped during the static recovery step for a period of time that is sufficient to allow permeate to remove a desired amount of target protein from the membrane surfaces, typically at least about 5 to about 15 minutes. A person of ordinary skill in the art to which the invention pertains can readily determine a suitable duration for the static recovery step.

Methods of recovering proteins from the feed channel of a SPTFF assembly are known in the art and include, for example, flushing the feed channel with a liquid (e.g., water, buffer) or dispensing pressurized air through the feed channel, also known as an "air blow-down."

The permeate in the assembly can be liquid permeate or dry permeate (e.g., a dry air or vacuum permeate). When the permeate is a dry permeate, the process can further include the step of introducing a liquid (e.g., water, buffer) to the dry permeate to facilitate diffusion of the permeate through the filtration membranes.

Methods of Cleaning SPTFF Systems

Routine cleaning of TFF assemblies is required to prevent batch-to-batch carryover and restore the membrane for batch-to-batch process consistency. Batch systems recirculate cleaning agents through the system to ensure adequate cleaning. However, recirculation of cleaning agents cannot be employed for the SPTFF flow configuration without introducing a recirculation loop and taking away the simplicity and ease-of-use benefits of SPTFF. Accordingly, there is a need for improved methods of cleaning SPTFF assemblies that restore SPTFF assemblies to desired levels of cleanliness in the absence of recirculation of cleaning agents.

The present invention contemplates, in one embodiment, methods of cleaning SPTFF assemblies that include a static cleaning step. As used herein, "static cleaning step" refers to a step during which the pressurized flow of liquid through the SPTFF system is stopped to allow cleaning agent (e.g., NaOH) in the system to diffuse by osmosis throughout the TFF cassettes and the filtration membranes therein. As described herein, a cleaning method employing a static cleaning step has been used successfully to clean an SPTFF assembly after intravenous immunoglobulin (IVIG).

The static cleaning step has a duration (e.g., typically at least about 30 to about 60 minutes) that is sufficient to allow the cleaning agent to eliminate contaminants in the system (e.g., by hydrolysis). A person of ordinary skill in the art to which the invention pertains can readily determine a suitable duration for the static cleaning step.

In one embodiment, the invention provides a process for cleaning a TFF assembly (e.g., a SPTFF assembly, a batch TFF assembly), comprising the steps of flushing a liquid that lacks cleaning agent (e.g., water, buffer) through a feed channel in the TFF assembly for a period of time sufficient to allow the liquid to displace product from the surfaces of filtration membranes in the assembly and out of the feed channel; subsequently flushing the feed channel in the assembly with a cleaning solution comprising a cleaning agent, thereby removing the displaced product from the feed channel; stopping the flow of liquid through the assembly for a period of time sufficient to allow the cleaning agent to reach the internal surfaces of the assembly and diffuse into fouling deposits on the filtration membrane, thereby dissolving the fouling deposits; and flushing the assembly with a liquid that lacks the cleaning agent to remove residual cleaning agent from the assembly.

Exemplary methods for flushing a SPTFF assembly with a liquid (e.g., buffer, water, cleaning solution) are known in the art.

Persons of ordinary skill in this art can readily select an appropriate cleaning agent(s) for removing the particular type of contaminant(s) or foulant(s) (e.g., adsorbed protein, cell debris, lipids, polysaccharides, organic colloids, mineral deposits, metal complexes) that are sought to be removed from the membranes in the SPTFF system. Exemplary cleaning agents for SPTFF systems include, but are not limited to, NaOH, Tergazyme®, NaOCl, Triton® X-100, $H_3PO_4$, SDS, citric acid, $HNO_3$, Tween®-80, urea, and $HNO_3H_3PO_4$, as well as various combinations thereof. Preferably, the cleaning agent is NaOH (e.g., about 0.5 M NaOH).

In some embodiments, the method also comprises the step of testing the assembly to determine whether the surface of the filtration membranes has been restored to a desired level of cleanliness. Methods of testing SPTFF assemblies for cleanliness are known in the art and include, for example, measuring the normalized water permeability (NWP) of TFF cassettes and filter membranes. Techniques for assessing NWP are well known in the art. Alternatively and/or in addition, the cleanliness of a SPTFF assembly can be tested after cleaning by flushing the system with a solution (e.g., buffer, water) that lacks cleaning agent and assaying for residual carry-over protein.

Partial Recirculation TFF Methods of the Invention

The processes and methods of the invention described herein, can in some embodiments, be performed using partial recirculation TFF. Partial recirculation TFF relates to a method of filtering a liquid feed, comprising passing a liquid feed through a tangential flow filtration (TFF) system, recovering permeate and a portion of the retentate from the system in separate containers without recirculation through the TFF system, and recirculating the remainder of the retentate through the TFF system at least once. Recirculating all or a portion of the retentate during start up provides a method by which to ensure that the system has reached equilibrium and the retentate has achieved the desired concentration prior to collecting it into the product vessel. It also provides a convenient way to respond to system upsets during processing to provide a more robust process. The fraction of retentate that is recirculated can be adjusted via modulation of the pump or control valve as a way to tune the system in order to assure consistent retentate concentration and/or consistent retentate flow rate to the product collection vessel every run even if feedstock protein concentration, new membrane permeability, membrane fouling, membrane permeability, or membrane mass transfer or pressure drop varies from batch to batch. This strategy has particular benefits in the context of continuous processing where the success of subsequent operations rely on the output of a previous operation. Recirculation of retentate can improve cleaning effectiveness through increased cross flow velocity and reduce cleaning solution through recirculation. The TFF systems described above for use in the SPTFF methods of the invention typically are also useful for the TFF methods involving partial recirculation of retentate that are described herein. The TFF systems employed in the TFF methods of the invention involving recirculation additionally include at least one pump or control valve for recirculating retentate through all or part of the system and at least one conduit for recirculating (e.g., carrying) retentate.

Typically, in a TFF method involving partial recirculation of retentate, at least about 50% of the retentate is collected after a single pass, while the remainder of the retentate is recirculated. Preferably, about 10% or less (e.g., about 0.5%, about 1%, about 2%, about 5%, about 10%) of the retentate is recirculated after the first pass through the TFF system.

The amount of retentate that is recirculated can be controlled using, for example, a pump or a valve. A flow meter can be used to provide a process value for the pump or valve to control the amount of retentate that is recirculated. Thus, in some embodiments, the TFF systems described herein for use in the partial recirculation TFF methods of the invention can further comprise a valve or pump and/or a flow meter for controlling recirculation of retentate. Preferably, the valve or pump and/or flow meter is positioned on the retentate outlet or flow line carrying retentate out of the system to the retentate receptacle.

The retentate that is being recirculated can be returned to any upstream location in or before the TFF system. In one embodiment, the retentate is recirculated to the feed tank. In another embodiment, the retentate is recirculated to the feed line near the feed pump before the feed inlet on the TFF system.

TFF Diafiltration Methods of the Invention

In some embodiments, the processes and methods described herein further comprise performing diafiltration (e.g., to remove or lower the concentration of salts or solvents in the liquid feed, or to accomplish buffer exchange). In a preferred embodiment, the diafiltration is performed by concentrating the liquid feed (e.g., by TFF) to reduce the diafiltration volume and then restoring the feed to its starting volume by adding diafiltration solution, a process which is known in the art as discontinuous, or batch, diafiltration. In another embodiment, the diafiltration is performed by adding the diafiltrate solution to retentate to increase the diafiltration volume followed by concentrating the sample to restore it to its original volume. In yet another embodiment, the diafiltration is performed by adding the diafiltration solution to unfiltered feed at the same rate that permeate is removed from the TFF system, a process which is known on the art as continuous, or constant-volume, diafiltration. Suitable diafiltration solutions are well known and include, for example, water and various aqueous buffer solutions.

To perform diafiltration, the TFF system employed can include a reservoir or container for diafiltration solution and one or more conduits for carrying diafiltration solution from the diafiltration solution container to the liquid feed tank.

To avoid extremes of concentration and in-line dilution as part of the diafiltration process (e.g. >90%), it is preferred to inject the diafiltrate into multiple sections of the filtration assembly to restore the flow in the retentate section to the same flow as in the initial feed. This requires matching the rate of diafiltrate buffer addition with the rate of permeate removal. A preferred method is to use a single pump with multiple pump heads containing the diafiltrate addition and permeate removal flow lines (e.g. Peristaltic pump from Ismatec (Glattbrugg, Switzerland). Each pump head will have closely-matched pumping rates so this process will be balanced and maintain efficient buffer exchange. It is recommended to match flows for each of the multiple sections by using pumps containing up to 24 channels.

A description of example embodiments of the invention follows.

EXAMPLE 1

A Hybrid SPTFF System for Operation of Cassettes in Parallel and/or in Series A SPTFF model was developed to evaluate and compare conversion, permeate flow rate, and pressure drop for three cassettes staged in series and three cassettes staged in parallel. The model was based on the Pellicon® device format with 30 kD Ultracel membrane and C-screen (EMD Millipore). Experimental testing has indicated that feed flows of 0.25-0.5 LMM are typically required to achieve the target conversion or concentration. SPTFF flushing steps should be performed at higher flow rates to reduce time. Pumps used for large scale processing commonly have flow ranges of 6-10×. Given these considerations, a feed flow rate for flushing steps of 1 LMM was selected for this model. Each cassette was divided into 28 elements (~0.5 cm each). The properties of the fluid and cassette were assumed to be constant within each element. The output of element n was used at the input to element n+1. The lower limit of the model was defined as an outlet pressure 0 psig. The upper limit of the model was defined as 100% conversion (i.e. retentate flow rate=0). Additional model inputs are defined below:

Membrane Permeability: 10 LMH/psi
Viscosity=1 cPa
Pressure Drop per element=$(1.56*Q+0.255*Q^2)/28$
Note: Pressure drop based on internal Millipore experimental data.
Feed Flow Rate=1 LMM The permeate flush volume specification of 70 L/m2 for Pellicon® 2 devices (EMD Millipore) was used in this example. The total flush times were calculated for total conversions of 70%, 80%, 90%, and 100%. For the serial example, flush time was calculated based on the permeate flow rate of the third stage. The estimated permeate flow rates are shown in Tables 1 and 2. The comparison of estimated flush times is shown in Table 3.

TABLE 1

Expected Flushing Flow Rates For Cassettes Operated in Parallel

| Total Conversion (%) | Inlet Pressure (psig) | Outlet Pressure (psig) | Segment 1 Permeate Flux (LMH)[1] | Retentate Flux (LMH)[1] |
|---|---|---|---|---|
| 70 | 4.88 | 3.74 | 42.00 | 18.00 |
| 80 | 5.46 | 4.40 | 48.00 | 12.00 |
| 90 | 6.03 | 5.05 | 54.00 | 6.00 |
| 100 | 6.60 | 5.71 | 60.00 | 0.00 |

[1]Flux based on total system area (3X)

TABLE 2

Expected Flushing Flow Rates For Cassettes Operated in Series

| Total Conversion (%) | Inlet Pressure (psig) | Outlet Pressure (psig) | Segment 1 Permeate Flux (LMH)[1] | Segment 2 Permeate Flux (LMH)[1] | Segment 3 Permeate Flux (LMH)[1] | Retentate Flux (LMH)[2] |
|---|---|---|---|---|---|---|
| 70 | 10.30 | 0.61 | 74.49 | 36.61 | 14.90 | 18.00 |
| 80 | 10.66 | 1.72 | 78.36 | 42.05 | 23.58 | 12.00 |
| 90 | 11.03 | 2.81 | 82.28 | 47.54 | 32.19 | 6.00 |
| 100 | 11.44 | 4.00 | 86.70 | 53.70 | 39.61 | 0.00 |

[1]Flux based on area of individual stage (1X)
[2]Flux based on total system area (3X)

TABLE 3

Estimated Flush Times and Volumes for Serial and Parallel Cassette Processing

| | Parallel Operation | | Serial Operation | |
|---|---|---|---|---|
| Total Conversion (%) | Estimated Flush Time (hr) | Total Estimated Flush Volume (L/m²) | Estimated Flush Time (hr) | Total Estimated Flush Volume (L/m²) |
| 70 | 1.67 | 100.00 | 4.70 | 281.82 |
| 80 | 1.46 | 87.50 | 2.97 | 178.09 |
| 90 | 1.3 | 77.78 | 2.17 | 130.48 |
| 100 | 1.17 | 70.00 | 1.77 | 106.05 |

Although serial processing shows an overall improvement in conversion with proteins, it requires additional time and volume to flush the cassettes compared to parallel processing. Additional process time and volumes increases the overall cost of the unit operation. The above example is specific to initial pre-use preservative flushing, but the challenges associated with flushing cassettes staged in series will be consistent for all flushing steps. It is especially critical to ensure proper flushing when cleaning to ensure adequate exposure to cleaning solution. Since conversion and expected protein concentration will be highest in the final processing unit, the final processing unit is typically the most challenging to effectively clean. The final processing unit is also the most difficult to flush. It is critical to ensure proper flushing of this final processing unit during cleaning.

Large scale SPTFF installations with cassettes processed in series are expected to have a common permeate line. The permeate from all processing units feed a common manifold preventing operators from measuring the flow rates for individual units. When measuring normalized water permeability (NWP), the TMP and average cross flow rate will decrease for later units which can hinder water permeability measurements and prevent proper assessment of cleaning effectiveness. If cleaning solution is not adequately flushed through the third unit causing ineffective cleaning, it may be difficult to determine.

EXAMPLE 2

Effectiveness of a Cleaning Method for TFF Cassettes Employing Parallel Flushing and a Static Soak Step A study was carried out to evaluate the effectiveness of cleaning TFF cassettes by employing a static soak step with 0.5N NaOH over 20 SPTFF re-uses of the cassettes. Pellicon® 3 C-screen mini cassettes with 30 KD Ultracel membranes were used for this study. The TFF cassettes were incorporated into a hybrid SPTFF system of the invention that was capable of being operated in series or in parallel. The cassettes were cleaned by flushing in parallel and soaking with 0.5N Sodium Hydroxide (NaOH) for 20 cycles. One additional cycle was carried out to flush the cassettes in series to simulate a SPTFF set-up where cleaning in parallel was not feasible. This was done to determine if there is any difference in the cassettes' performance recovery between flushing the cassettes in parallel and series. IgG (SeraCare Life Sciences, Inc., Milford, Mass.) was used as model feed. A full 4-hour SPTFF process was run before each cleaning cycle.

Twenty (20) cycles over a 4-hour duration were conducted at 75 ml/min (0.2 LMM) at a protein concentration range of 120-150 g/L to meet process scale conditions. Retentate pressure was controlled at 10-15 psi and process flux was measured to check for process reproducibility. The cleaning cycle consisted of flushing 0.5N NaOH in parallel at a feed flow rate of 450 ml/min (1.4 LMM) for 15 minutes followed by soaking 0.5N NaOH for 45 minutes. Following each cleaning cycle, purified flush water Total Organic Carbon (TOC) was tracked in permeate line and Normalized Buffer Permeability (NBP) was measured.

The effectiveness of the cleaning cycles was evaluated and compared using the following criteria:
  Process Normalized Buffer Permeability (NBP)—measured in parallel flow configuration
  Process flux, conversion and pressure drop;
  Product retention; and
  Residual Total Organic Count (TOC) in Post Cleaning Water Flush.

Figure 8:
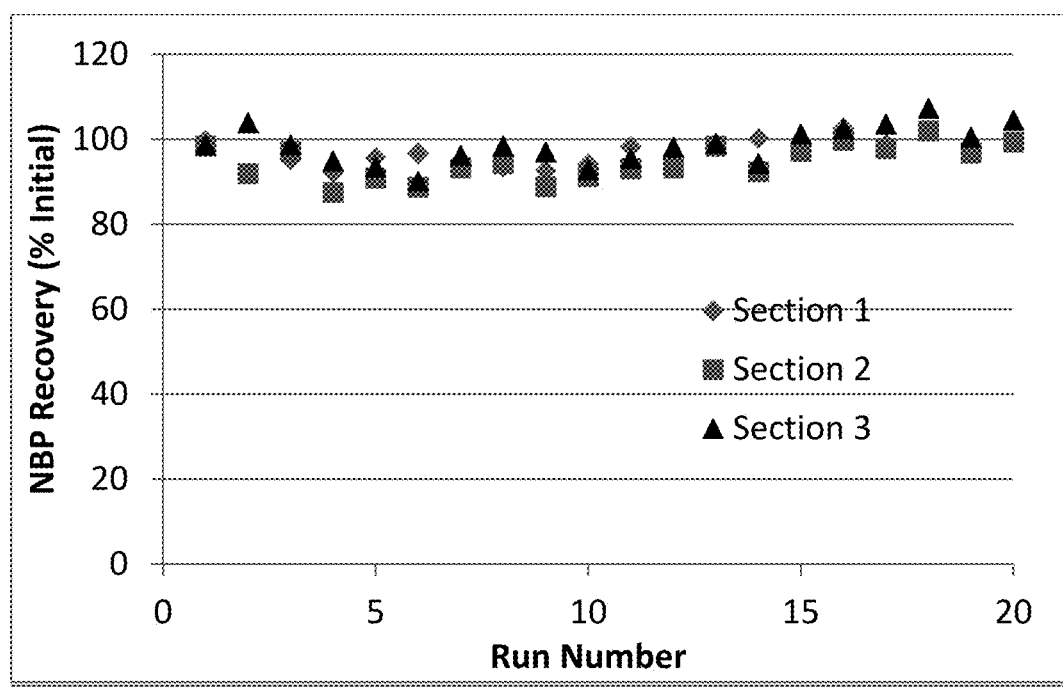
FIG. 8 shows Normalized Buffer Permeability (NBP) recovery after static soak cleaning.

The recovery of NBP is shown in FIG. 8. The NBP of the individual sections is plotted to better show cleaning effectiveness. The test results showed that this static soaking cleaning method is effective to restore the membrane performance with more than 90% NBP recovery after every cleaning cycle.

Figure 9:
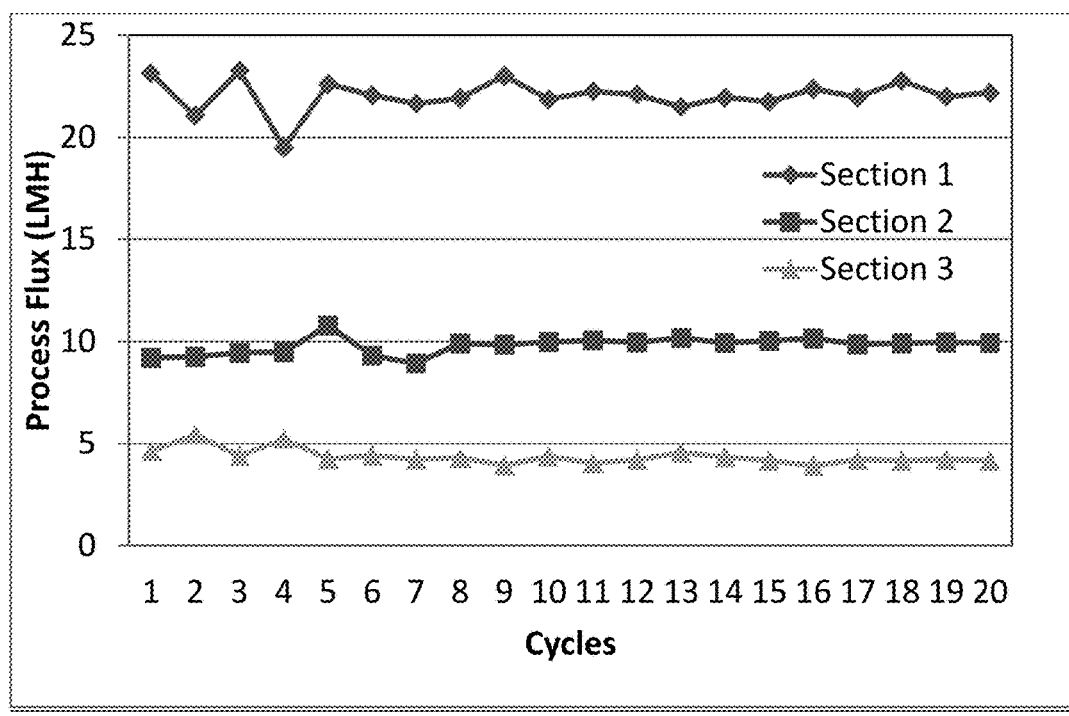
FIG. 9 shows the process flux after re-use with static soak cleaning.

The process flux after re-use with static cleaning is shown in FIG. 9. The process flux of the individual sections is plotted to better show cleaning effectiveness.

The cassettes demonstrated reproducible process flux for all three stages in the 20 cycles of concentration.

Additionally, the process maintained >99.8% protein retention throughout the cleaning evaluation. All flush TOC samples after the cleaning cycles showed less than 1 ppm TOC.

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A single-pass tangential flow filtration (SPTFF) assembly, comprising:
   a plurality of stacked processing units that are fluidly connected, wherein each processing unit comprises a cassette holder containing a first channel, a second channel and a permeate channel and at least one TFF cassette, and wherein the processing units in the assembly are configured for processing in parallel and/or in series;
   wherein the first channel, the second channel and the permeate channel of adjacent stacked cassette holders in the processing units are fluidly aligned such that
   the first channel connected to a feed inlet extends through each cassette holder of the plurality of processing units;
   the second channel connected to a retentate outlet extends through each cassette holder of the plurality of processing units;
   the permeate channel extends through each cassette holder of the plurality of processing units; and
   one or more valves, wherein each valve is located on either the first channel or the second channel between two adjacent cassette holders in the processing units, and wherein the valves alternate between the first channel and second channel for consecutive pairs of cassette holders in adjacent processing units;
   wherein the plurality of processing units are processed in parallel when the valves are open, or in series when the valves are closed.

2. The SPTFF assembly of claim 1, further comprising 1) a spool piece on the second channel between each pair of adjacent processing units having a valve on the first channel; or 2) a spool piece on the first channel between each pair of adjacent processing units having a valve on the second channel.

3. The SPTFF assembly of claim 1, wherein 1) the plurality of processing units are stacked vertically; 2) the assembly contains two processing units; 3) the assembly contains three processing units; or 4) the assembly contains more than three processing units.

4. The SPTFF assembly of claim 1, wherein 1) the valves are sanitary valves; or 2) the valves are built into the cassette holders.

5. The SPTFF assembly of claim 1, wherein the SPTFF assembly is a disposable single-pass tangential flow filtration assembly (SPTFF) comprising disposable components, wherein the disposable components include:
   a disposable feed line in fluid connection with the first channel;
   the at least one TFF cassette being a disposable TFF cassette;
   the holder for the at least one TFF cassette;
   a disposable retentate line in fluid connection with the second channel; and
   the one or more valves being disposable,
   wherein fluid contact surfaces on the disposable components are contained in a sealed disposable container that comprises tubing for making aseptic connections to feed and product vessels.

6. The SPTFF assembly of claim 5, wherein 1) the one or more disposable components are made from plastic; or 2) the one or more disposable components are replaceable.

7. The SPTFF assembly of claim 5, comprising a plurality of TFF cassettes and holders, wherein the holders are stacked to produce a stacked assembly.

8. The SPTFF assembly of claim 5, comprising a plurality of disposable holders, wherein the holders are fluidly connected in parallel.

9. The SPTFF assembly of claim 5, wherein the retentate line further comprises a T-line for in-line buffer addition.

10. The SPTFF assembly of claim 5, further comprising at least one of: 1) a disposable pressure sensor; 2) a disposable diaphragm for a pressure sensor; 3) one or more retentate end plates for a stacked assembly, wherein the retentate end plates are disposable; and 4) a disposable bioprocess container for feed in a mechanical support that allows pressurization.

11. A process for recovering proteins from the surface of a filtration membrane in a single-pass tangential flow filtration (SPTFF) assembly, comprising:
   a) introducing a liquid feed comprising proteins into a feed channel in the FF assembly of claim 1;
   b) passing the liquid feed across a filtration membrane along the feed channel, thereby separating the liquid feed into a retentate and a permeate;
   c) stopping the flow of the liquid feed across the membrane for a period of time sufficient to allow permeate to diffuse backwards through the membrane by osmosis, thereby displacing proteins from the surface of the membrane back into the feed channel; and
   d) recovering the displaced proteins from the feed channel.

12. The process of claim 11, wherein the proteins are recovered from the feed channel by flushing the feed channel with a liquid; or the proteins are recovered from the feed channel by dispensing pressurized air through the feed channel.

13. The process of claim 11, wherein the permeate is a dry air or vacuum permeate and liquid water is introduced into the permeate to promote osmosis in (c).

14. A process for cleaning a single-pass tangential flow filtration (SPTFF) assembly, comprising:
   a) flushing a liquid that lacks cleaning agent through a feed channel in the SPTFF assembly of claim 1 for a period of time sufficient to allow the liquid to displace product from the surfaces of filtration membranes in the assembly to the feed channel;
   b) flushing the feed channel in the assembly with a cleaning solution comprising a cleaning agent, thereby removing the displaced product from the feed channel;
   c) stopping the flow of liquid through the assembly for a period of time sufficient to allow the cleaning agent to reach the internal surfaces of the assembly and diffuse into fouling deposits on the filtration membrane, thereby dissolving the fouling deposits; and
   d) flushing the assembly with a liquid that lacks the cleaning agent to remove residual cleaning agent from the assembly.

15. The process of claim 14, wherein the assembly is a single-pass TFF assembly or a batch TFF assembly.

16. The process of claim 14, further comprising testing the assembly to determine whether the surface of the filtration membrane has been restored to a desired level of cleanliness.

17. The process of claim 14, wherein the cleaning agent is NaOH.

18. A method of installing a disposable single-pass tangential flow filtration (SPTFF) assembly, comprising:
  a) establishing a first aseptic connection between a feed line of a disposable SPTFF assembly of claim 5 and a feed container; and
  b) establishing a second aseptic connection between a retentate line of the disposable SPTFF assembly and a product container.

19. A method of increasing the processing capacity of a single-pass tangential flow filtration (SPTFF) assembly, comprising:
  a) increasing the filtration membrane area in the SPTFF assembly of claim 1; and
  b) increasing the volumetric flow of feed solution that is being delivered to the SPTFF assembly to a level that is proportional to the increase in filtration membrane area;
  wherein the residence time of the feed solution and the length of the flowpath in the SPTFF assembly are maintained.

20. The method of claim 19, wherein the filtration membrane area in the assembly is increased by 1) replacing at least one TFF cassette in the assembly with a larger TFF cassette; or 2) adding at least one TFF cassette to the assembly.

21. A tangential flow filtration (TFF) assembly, comprising:
  a plurality of stacked processing units that are fluidly connected, wherein each processing unit comprises a cassette holder containing a first channel, a second channel and a permeate channel and at least one TFF cassette, and wherein the processing units in the assembly are configured for processing in parallel and/or in series;
  wherein the first channel, the second channel and the permeate channel of adjacent stacked cassette holders in the processing units are fluidly aligned such that
  the first channel connected to a feed inlet extends through each cassette holder of the plurality of processing units;
  the second channel connected to a retentate outlet extends through each cassette holder of the plurality of processing units;
  the permeate channel extends through each cassette holder of the plurality of processing units;
  at least one pump or control valve for recirculating retentate through all or part of the assembly;
  at least one conduit for recirculating retentate; and
  one or more valves, wherein each valve is located on either the first channel or the second channel between two adjacent cassette holders in the processing units, and wherein the valves alternate between the first channel and second channel for consecutive pairs of cassette holders in adjacent processing units;
  wherein the plurality of processing units are processed in parallel when the valves are open, or in series when the valves are closed.

* * * * *

UNITED STATES PATENT AND TRADEMARK OFFICE
CERTIFICATE OF CORRECTION

PATENT NO. : 10,207,225 B2
APPLICATION NO. : 14/736646
DATED : February 19, 2019
INVENTOR(S) : Herbert Lutz, Joseph Parrella and Bala Raghunath It is certified that error appears in the above-identified patent and that said Letters Patent is hereby corrected as shown below:

In the Claims

In Column 22, Claim 11, Line 29 delete "FF" and insert --SPTFF--

Signed and Sealed this
Seventh Day of May, 2019

Andrei Iancu
*Director of the United States Patent and Trademark Office*